(12) United States Patent
Attia

(10) Patent No.: US 9,125,872 B2
(45) Date of Patent: Sep. 8, 2015

(54) POLYETHYLENE GLYCOL AEROGELS FOR TARGETED DELIVERY OF PHARMACEUTICAL DRUBS

(76) Inventor: Yosry A. Attia, Delaware, OH (US)

( * ) Notice: Subject to any disclaimer, the term of this patent is extended or adjusted under 35 U.S.C. 154(b) by 910 days.

(21) Appl. No.: 12/902,184

(22) Filed: Oct. 12, 2010

(65) Prior Publication Data

US 2011/0086100 A1  Apr. 14, 2011

Related U.S. Application Data

(60) Provisional application No. 61/250,928, filed on Oct. 13, 2009.

(51) Int. Cl.
| | |
|---|---|
| A61K 9/14 | (2006.01) |
| A61B 5/055 | (2006.01) |
| A61K 31/16 | (2006.01) |
| A61K 9/51 | (2006.01) |
| A61K 9/70 | (2006.01) |
| A61K 31/337 | (2006.01) |
| A61K 31/351 | (2006.01) |
| A61K 31/40 | (2006.01) |
| A61K 31/4375 | (2006.01) |
| A61K 31/4439 | (2006.01) |
| A61K 31/573 | (2006.01) |
| A61K 31/7048 | (2006.01) |
| A61K 31/7068 | (2006.01) |
| A61K 47/10 | (2006.01) |
| A61K 49/18 | (2006.01) |

(52) U.S. Cl.
CPC .............. *A61K 31/16* (2013.01); *A61K 9/5146* (2013.01); *A61K 9/5192* (2013.01); *A61K 9/7007* (2013.01); *A61K 31/337* (2013.01); *A61K 31/351* (2013.01); *A61K 31/40* (2013.01); *A61K 31/4375* (2013.01); *A61K 31/4439* (2013.01); *A61K 31/573* (2013.01); *A61K 31/7048* (2013.01); *A61K 31/7068* (2013.01); *A61K 47/10* (2013.01); *A61K 49/1803* (2013.01)

(58) Field of Classification Search
CPC . A61K 49/1803; A61K 9/5146; A61K 47/10; A61K 31/7048; A61K 31/4439; A61K 31/7068
USPC .......................................................... 424/484
See application file for complete search history.

(56) References Cited

U.S. PATENT DOCUMENTS

| | | | |
|---|---|---|---|
| 6,994,842 B2 * | 2/2006 | Lee et al. ........................ 424/45 |
| 2007/0128681 A1 * | 6/2007 | Barman et al. .................. 435/14 |
| 2009/0082479 A1 * | 3/2009 | Cho .............................. 521/141 |
| 2011/0056408 A1 * | 3/2011 | Schaumburg et al. ..... 106/18.32 |

OTHER PUBLICATIONS

Popat et al., 2004, Langmuir 20:8035-80411.*
Nagahma et al 2009, Langmuir 25:9734-9740.*
Zustiak et al Jan. 2011, Biotechnol. Bioeng. 108:197-206.*
Cho et al 2009, J. Biomed. Mater. ResA. 15:90(4):1073-1082.*

* cited by examiner

*Primary Examiner* — Christopher M Babic
*Assistant Examiner* — Kelaginamane T Hiriyanna
(74) *Attorney, Agent, or Firm* — Mueller Law, LLC; Jerry K. Mueller, Jr.

(57) ABSTRACT

A polyethylene glycol (PEG) aerogel particles having an average particle diameter not substantially above about $2\mu$, a volumetric porosity of greater than about 50%, and pore sizes capable of retaining drug molecules. A method for preparing such polyethylene glycol (PEG) aerogel particles includes initiating a catalyzed reaction using a catalyst of PEG forming ingredients to form PEG particles; partially drying the formed PEG particles under conditions to control pore size; and subjecting the partially dried formed PEG particles to $CO_2$ supercritical extraction for form the PEG aerogel particles. Drug molecules include chemotherapeutic agents. The surface of the PEG aerogel particles are reactable with a variety of agents, for example, to selectively target tumors, protects irreversible damage to labile proteins, and protects degradation of sensitive drugs with subsequent loss of biological efficacy.

4 Claims, No Drawings

POLYETHYLENE GLYCOL AEROGELS FOR TARGETED DELIVERY OF PHARMACEUTICAL DRUBS

CROSS-REFERENCE TO RELATED APPLICATIONS

This application claims benefit of provisional application Ser. No. 61/250,928, filed on Oct. 13, 2009.

STATEMENT REGARDING FEDERALLY SPONSORED RESEARCH

Not applicable.

BACKGROUND

Aerogels are three-dimensional network of nanophase architecture composed of gas [usually air] and solid structure, with air [gas] to solid ratio of 60-98% by volume. Thus aerogels have high porosity, high specific surface area, and very low density. Aerogels can be made as large monolithic shapes, or micron/submicron size bodies, or any size and shape in between. The gas inside the aerogel nanostructures can be replaced [displaced] with other substances, such as, for example, pharmaceuticals, which then are released into the desired targets in a controlled manner. Further, incorporation of targeting proteins/agents, such as, for example, EGF [epidermal growth factors for cancer cells] into the aerogel structure and loading the aerogel nano-chambers [pores] with a medication, such as, for example, Paclitaxel or melittin, makes it possible to deliver the drug selectively and specifically to cancer tumors, rather than indiscriminately to all cells. Thus, only cancer cells would be destroyed without any significant side effects to healthy cells.

Aerogels made from PEG [polyethylene glycol] are non-toxic, biocompatible with "stealth" properties to prolong their stay in blood stream and biodegradable with no harmful side effects. This makes them an excellent choice for use in biomedical applications. Indeed, PEG is widely used in the pharmaceutical industry because of its non-toxic and non-immunogenic properties. In addition to its excellent tolerance in humans, PEG stabilizes the physiological function of proteins and bioactive substances. However, and unlike nanoparticles and other drug carriers, aerogels can contain much larger volumes of drugs inside their structure and, thus, the drugs are protected until they reach their intended targets.

Examples of the drugs that can benefit from encapsulation or incorporation in PEG aerogels include, for example, poorly water soluble drugs such as, for example: Paclitaxil, alprostadil, amphotericin B, camptothecin, cosalane, chloramphenicol, cyclosporine, iovastatin, omeprazole, dexamethasone, HIV-1 protease inhibitors, hydroxycortosone, indomethacin, phenytoin, and tolbutaide; and proteins of different sizes and stabilities, such as, for example, insulin-5700, IgG-150,000, and interferon.

Prior proposals in the field include U.S. Pat. Nos. 5,869,545, 6,475,516, 6,623,729, 6,703,047, 6,890,560, 6,994,842, 7,018,645, 7,135,190, 7,589,157, 7,648,713, 7,732,427, and 7,731,988; published applications 2009/0291115, 2010/0112057; EP No. 0130577 and 1019446; AUS 9,965,549 and 711,078; and Smirnova, et al., "Feasibilty of hydrophilic and hydrophobic silica aerogels as drug delivery systems", *Journal of Non-Crystalline Solids,* 350 (2004) 54-60.

BRIEF SUMMARY

Development of new methods for producing PEG-only aerogel products for safe and effective delivery of targeted cancer therapeutics as well as delivery of other important drugs include:

(a) Preparation of PEG aerogel micro particles [2 microns or less], with high volume porosity [up to 90%], and varied pore sizes from 20-200 nm.

(b) Incorporation of EGF [Epidermal Growth Factor] proteins into the PEG aerogel micro-particles with variable EGF to PEG ratios [up to 50% or more surface coverage and ranging from about 50% to about 99%].

(c) Preparation of Paclitaxil-encapsulated PEG-EGF aerogel dry particles with minimal degradation of the drug [as low as 2%].

Drug delivery for present purposes is designed for use with animals, including veterinary animals and humans.

A new procedure for preparation of in situ produced micro alcogel-PEG particles, which after appropriate drying method for removal of interstitial liquids (alcohol) without collapsing the 3-D gel pore structure, become micro aerogel particles. This method produces more rounded (spherical) particle shapes, which are more suitable for intravenous injection than milling/grinding of dry aerogel by mechanical means, which produce irregular and jagged shapes.

These micro alcogel particles are formed by high shear mixing of sol-gel reacted alcogel in a suspending liquid (such as ethyl alcohol) containing surface coating anionic dispersants, such as, for example, sodium hexa-meta-phosphate at pH 8 to help inhibit newly formed nano alcogel particles from re-gelling or agglomerating into larger gel particles. The suspending liquid also contains amino PEG for coating the surface of the gel particles with a "stealth" layer through surface adsorption mechanisms. The suspending liquid is removed (e.g., by decantation after a prolonged settling time), before gel particles are placed in an autoclave for drying by $CO_2$ supercritical extraction.

The chemical composition of PEG-containing aerogel selected in this case includes, for example, MgO, CaO, $SiO_2$, $Gd_2O_3$, or amino PEG. Precursors of these ingredients were mixed together at gel preparation step. Thus, these aerogel micro particles contain amino PEG in the structure as well as adsorbed on their surface. These aerogel particles are now ready for attachment of EGF proteins onto them via reaction between aerogel anchored/adsorbed amine groups in PEG and EGF's amino acid groups. Alternatively, EGF proteins may be directly incorporated into the aerogel structure during the gel formation steps in a similar manner to incorporation of the amino-PEG mentioned above.

This type of aerogel ($SiO_2$.MgO:CaO) previously developed has a distinct tendency to have majority of pores in macropore range [500-10,000 Å; 50-1000 nm] and to a lesser extent in the mesopore range [20-500 A; 2-50 nm], thus facilitating the storage and release of large volumes of large molecules, such as melittin.

A cancer cell targeting proteins (EGF, epidermal growth factors) are attached onto the nano aerogel particle via surface reactions between EGF proteins' amino acid groups and aerogel-anchored amino group. As mentioned earlier, these EGF proteins may also be incorporated into the particle during gel formation. The nano aerogel particles, which now are stealth coated, containing ($Gd_2O_3$) identification labels and targeting proteins (EGF) for cancer cells are then filled with melittin and readied for direct injection or for storage until use.

Advantages of the disclosure include production of in situ biocompatible nano-aerogel particles of less than 2 microns in average particle diameter with up to about 95% porosity, and pore sizes large enough for large medicine molecules, such as, for example, militin, and anchoring sites for targeting proteins. The disclosed particles have the following features: high drug volume loading of PEG aerogel particles, selectivity/specificity of the drug loaded PEG aerogel particles for target cells of interest, controlled release profile of drug from the drug loaded PEG aerogel particles, and inertness of the drug loaded PEG aerogel particles. The PEG particles may be coated to achieve a variety of special affects: delayed release, controlled drug delivery, selective binding to target cells by incorporation of EGF (Epidermal Growth Factor) with variable EGF to PEG ratios (up to 50% or more surface coverage); and preparation of Paclitaxel-encapsulated PEG-EGF aerogel dry particles with minimal degradation of the drug (as low as 2%). These and other advantages will be apparent to the skilled artisan based on the instant disclosure.

DETAILED DESCRIPTION

This disclosure relates to methods for preparation of PEG only aerogels and PEG-containing aerogels for intravenous (or other suitable administration) delivery of drugs to treat only target cells that are inflected by the disease in question. These methods prepare very small aerogel particles [e.g., less than 2 microns] with high volume porosity [e.g., up to 95% or more] and are biocompatible to prolong their unimpeded circulation in blood [either (a) coated by a "stealth" material that makes them unrecognizable as foreign bodies by blood cells, or (b) made directly from biocompatible precursors], and either (a) contain anchoring sites for later attachments of cell-specific targeting proteins, or (b) directly incorporate these cell-specific targeting proteins into their aerogel structures. In addition, these aerogel particles also may incorporate identification labels into their structure, so their migration through the body can be monitored by appropriate diagnostic instruments. These biocompatible nano aerogel particles after having attached targeting proteins then are ready to be filled with treatment drug of choice and injected into patient's blood stream, where their "seek & destroy" missions begin.

PEG-Only Aerogels

Aerogels were prepared completely from PEG molecules chains for evaluation as a drug delivery platform. As mentioned earlier, aerogel materials have very high surface areas and open pore architecture that make them ideal drug carriers. Incorporation in PEG aerogels of the specific targeted delivery, for example, EGF, Paclitaxil, or other therapeutic drugs to cancer tumors, should be possible through "PEGylation" of EGF proteins or other possible routes. One-step preparation of PEG aerogel-encapsulated drugs, such as, for example, Paclitaxil, with or without EGF, as dry powders for long-term storage also is being considered for development. PEG-aerogel manufacturing is relatively inexpensive and should allow ultra-high levels of drug incorporation.

Preparation of PEG Aerogel Micro-Particles

PEG aerogels have been successfully produced in sheet format by two different methods of wet gel preparation, each was later dried by $CO_2$ supercritical solvent extraction. The "hot" method, where a high temperature (>70° C.) catalyst was used for gel formation, produced an aerogel with close to 80% porosity, and the "cold" method, using "room temperature" (25°-35° C.) gelation catalyst produced an aerogel with about 60% porosity. The sheet form was selected initially for ease of physical measurements. However, for the production of micro particles of PEG aerogels, the following options are possible: (a) micronization of sheet or large aerogel bodies, (b) micronization of wet gel before supercritical drying, and (c) spray drying of wet gel into supercritical drying autoclave. Fractionation of the aerogel particles into desired mono-sized fractions [e.g., 1-2 microns, or less than 1 micron] may be conducted using various techniques, such as, for example, gravitational settling, centrifuging, or fluid flow fractionation technique. Surface coating of PEG aerogel particles for the purpose of delayed release can be achieved through adsorption of polymeric molecules, such as, for example, PEG, from solutions. Production of PEG aerogel particles with 90% or better volume porosity and pore sizes from 20-200 nm should be possible through controlling different process parameters, and molecular weight of PEG.

Preparation of PEG Aerogels Incorporating EGF Proteins

Polyethylene glycol provides readily available sites for surface treatments or bio conjugation without steric hindrance. "PEGylation" of therapeutic proteins is well studied in the literature. Possible incorporation methods of EGF [epidermal growth factor] proteins into PEG aerogels include, for example: (a) physical incorporation into the aerogel structure, (b) use of "PEGylation" techniques to attach EGF to aerogel surfaces, (c) use of "star" or highly branched PEG into PEG aerogels to enhance EGF attachment concentration on aerogel particles, or (d) use of already "PEGylated" EGF in aerogel preparation.

Preparation of PEG/EGF Aerogel Particles Encapsulating Paclitaxil as Dry Powder

PEG-EGF aerogel or wet gel (before drying) particles are suspended in an ethanol or other solvent solution of Paclitaxil at pre-determined concentrations and dried to powder by supercritical $CO_2$ solvent extraction method. Paclitaxil also might be included during the PEG gelation process, provided that no significant degradation of the drug takes place.

PEG-Containing Aerogels

A goal of this disclosure was to develop very fine PEG-containing aerogel particles [e.g., less than 2 microns] of prepared SCM-PEG aerogel for the storage and subsequent controlled release of targeted pharmaceutics (such as, for example, melittin) therapy. The aerogel microparticles also incorporate a PEG "stealth" surface coating on it, such as, for example, o,o-Bis(3-aminopropyl) polyethylene glycol [referred to here as amino-PEG for short], which prolongs circulation of micro aerogel particles in the blood. The micro aerogel particles also would have anchoring chemical groups for the attachment of specific targeting proteins for the diseased cells, such as, for example, EGF proteins for cancer tumors. Also incorporated into the aerogel structure is, for example, gadolinium oxide, $Gd_2O_3$ [gadolinia], which acts as an identification label so the device can be tracked in the body.

In the examples in this disclosure, the prepared biocompatible PEG-containing micro aerogel particles, having ~90% volume porosity with gadolinium oxide aerogel, have been tested on cell lines, after attachment of cancer cell-targeting EGF proteins, and filling them with melittin [14]. The controlled release tests showed that over 97% of cancer cells were destroyed, with only 1% of non-cancer cells co-destroyed.

Cytotoxic/Chemotherapeutic Agents

The cytotoxic or chemotherapeutic agents include, but are not limited to, an antimicrotubule agent, a topoisomerase I inhibitor, a topoisomerase II inhibitor, an antimetabolite, a mitotic inhibitor, an alkylating agent, an intercalating agent, an agent capable of interfering with a signal transduction pathway (e.g., a protein kinase C inhibitor, e.g., an anti-hormone, e.g., an antibody against growth factor receptors), an agent that promotes apoptosis and/or necrosis, an interferon, an interleukin, a tumor necrosis factor, and/or radiation.

Exemplary cytotoxic agents include, but are not limited to, paclitaxel, vincristine, vinblastine, vindesine, vinorelbin, docetaxel, topotecan, camptothecin, irinotecan hydrochloride, doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytosine arabinoside, trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside, cladribine, ftorafur, UFT (combination of uracil and ftorafur), 5-fluoro-2'-deoxyuridine, 5'-deoxy-5-fluorouridine, tiazofurin, Xeloda (Capecitabine), cisplatin, carboplatin, oxaliplatin, mitomycin C, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldanamycins, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl)propionanilide, Herceptin, anti-CD20 (Rituxan), C225, Iressa, alpha, interferon beta, interferon gamma, interleukin 2, interleukin 4, interleukin 12, tumor necrosis factors, and radiation.

Examples of additional agents include, but are not limited to, hydroxyurea, azathioprine, aminopterin, trimethoprin, pyrimethamine, pyritrexim, DDMP (2,4 diamino-5(3',4' dichlorophenyl)6 methylpyrimidine), 5,10-dideazatetrahydrofolate, 10-propargyl-5,8 dideazafolate (CB3717), 10-ethyl-10-deaza-aminopterin, deoxycytidine, 5-aza-cytosine arabinoside, N-4-palmitoyl-ara C, 2'-azido-2'-deoxy-ara C, N4-behenoyl-ara C, CCNU (lomustine), estramustine, MeCCNU, triethylene melamine, trenimon, dimethyl busulfan, streptozotocin, chlorozotocin, procarbazine, hexamethylmelamine (Altretamine), pentamethylmelamine (PMM), tetraplatin, oxaliplatin, platinum-DACH, aziridinylbenzoquinone (AZQ), bleomycin, tallysomycin $S_{10}^b$, liblomycin, pepleomycin, asparaginase (Elspar), pegaspargase (Oncaspar), Cladrabine (leustatin), porfimer sodium (Photofrin), amonofide, deoxyspergualin, dihydrolenperone, flavone acetic acid, gallium nitrate, and hexamethylene bisacetamine (HMBA).

RNA interference (RNAi) holds promise for treating patients with diseases that are associated with over-expression of faulty genes or over-production of disease-causing proteins. RNAi is a cellular post-transcriptional gene silencing process for the targeted destruction of single-stranded RNA, such as a messenger RNA (mRNA). There are two types of RNAi, small interfering RNA (siRNA) and microRNA (miRNA).

DETAILED PREPARATIONS AND EXAMPLES

Example 1

Preparation of PEG Aerogels

Preparation of PEG only aerogel involve preparation of dilute solutions of polyethylene glycol in an organic solvent, typically 1-10 wt %., at elevated temperature [typically 125° C.] under reflux with moderate mixing. Warm peroxide catalyst solution is prepared by dissolving a peroxide compound, such as benzoyl peroxide, in a small volume of same organic solvent. The amount of catalyst used is proportional to the amount of PEG used in the solution and normally range between 2-20 wt %., but 10% is preferable. The catalyst solution is added to the PEG polymer solution while mixing and heating continues for further 15 minutes. Gel solution is poured into a mold and allowed to cool to room temperature. An optional step is to partially reduce solvent volume by evaporation before the drying step. Drying is accomplished by removing the organic solvent via solvent exchange with carbon dioxide supercritical fluid at 35° C. to obtain dry solid PEG aerogel.

In preparation of PEG aerogel #2, synthesis, the temperature was kept at 30° C. throughout and a room temperature catalyst [ethyl methyl ketone peroxide] was used. Since PEG is soluble in a wide variety of organic solvents, a number of solvents may be used in gel preparation. However, anhydrous toluene was used mostly in these preparations. Additionally, anhydrous ethanol also was used in the PEG gel preparation, even though PEG is insoluble in ethanol at room temperature, it is soluble in hot [125° C.] ethanol. On cooling the hot PEG ethanol solution, PEG did not precipitate and remained in solution.

A wide variety of original and modified PEG may be used in aerogel preparations. Examples of PEG aerogel preparations and their characteristics are shown in Table 1 below.

TABLE 1

Preparation and Characterization of Example PEG Aerogels

| No. | Peg Type & MW | Aerogel Density (g/cc) | Pore Volume (cc/g) | Porosity (% Volume) |
|---|---|---|---|---|
| 1 | PEG, 2,000,000 | 0.265 | 2.94 | 78 |
| 2 | PEG, 2,000,000 | 0.52 | 1.09 | 57 |
| 3 | PEG, 2,000,000 + BSA, 66,000 | 0.3 | 2.5 | 75 |
| 4 | PEG, 2,000,000 + Diglycidyl Ether-PEG, 1000 + Gadolinium DTPA* | 0.31 | 2.6 | 78 |
| 5 | PEG, 4,000,000 | 0.23 | 3.5 | 81 |
| 6 | PEG, 4,000,000 + [PEG-bis(3-aminopropyl) terminated], 2,100 | 0.31 | 2.6 | 81 |

*Diethylene Triamine Penta Acetic Acid, Gd (III)-Dihydrogen salt hydrate (97%).

Encapsulation of Biologics in PEG Aerogel During Gelation Strategy

BSA [bovine serum albumin, MW=66,000 Daltons] was used in the encapsulation as an example of a large biologic molecule that might be encapsulated in a PEG aerogel structure. Since BSA is sensitive to heat and chemical oxidation-reduction processes, care must be taken to avoid its integrity and functionality. BSA denaturation is reversible with heat up to 65° C. Above this temperature, irreversible denaturation takes place. Thus, PEG gelation reactions should be conducted preferably at room temperature and definitely below 65° C. Further, to avoid or minimize undesirable oxidation-reduction of BSA during gelation at room temperature, protective measures for BSA should be taken.

In this work, to minimize or avoid undesirable changes on BSA the following steps are taken:
1. Encapsulation of BSA as solid powder; not soluble molecules. Thus, any reactions would be limited to solid particle surface, while protecting the molecules in the solid particle core.

2. Coating of BSA powder/particle in suspension with a layer of soluble polyethylene glycol molecules.

3. Conducting PEG gelation reactions preferably at room temperature or well below 65° C. Room temperature catalysts, such as those containing ethyl methyl ketone peroxide, also may contain metal oxides such as cobalt oxide to activate the formation of free radicals necessary for catalysis. Presence of metal oxide may not be desirable to have in the PEG aerogel structure. Benzoyl peroxide, which is used for gelation/cross linking of PEG, may be used at room temperature with activation [decomposition and formation of free radical entities] by ultra-violet [UV] light source; otherwise, it is normally activated by heating above 75° C. In the absence of UV light source, benzoyl peroxide can be separately activated by heat, then added to PEG-BSA-solvent mixed suspension at lower temperature 35-40° C.

Encapsulation Procedure

To 1 gram PEG [MW=2,000,000] dissolved in 100 ml anhydrous toluene, 100 mg [0.1 gram] BSA powder is dispersed and the mixture was stirred at 38-45° C. for 30-60 minutes to allow coating/adsorption of soluble PEG molecules on solid BSA particles. 0.2 g benzoyl peroxide was heated in 15 ml anhydrous toluene at 85° C. for 10 minutes. After cooling to 76° C., the catalyst solution was added to the warm PEG-BSA suspension at 38° C., which raised the temperature to 43° C., and mixing was continued for 15 minutes. The solution was poured into a mold and stored in a glove box. Toluene was later removed from the gel by solvent extraction with supercritical carbon dioxide fluid to obtain dry solid aerogel encapsulating BSA fine particles.

Micronization and Size Fractionation of PEG Aerogel 0.5 grams of PEG aerogel #2 [density=0.52 g/cc] pieces were placed in a blender containing anhydrous ethanol and were ground/blended for 2 minutes. The PEG ethanol blend was poured into 1-liter beaker containing anhydrous ethanol so that the total height of the mixture was 5 cm. Using Stokes Law, the settling velocity for 2 micron and 1.75 micron PEG aerogel particles were calculated. Thus, for 1.75 micron PEG aerogel particles, the settling time for 5 cm was 19 hours and 14 minutes. After this time, the liquid was decanted which now contained particles less than 1.75 microns.

To verify this, 10 ml of the liquid was withdrawn and filtered in a membrane filter using 1.75 micron membrane. It was observed that no particles were retained on the filter and all particles passed through the filter, thus verifying that all remaining particles in suspension were less than 1.75 microns.

Example 2

Design Strategy of SCM-PEG Aerogel Micro Particles

Several reiterations of design strategies were considered, which finally culminated in having the gadolinium as an oxide in the overall aerogel structure, not as a gadolinium chelate, and incorporating the polyethylene glycol-amine compound both into the aerogel structure, and also on the outside surface. Several research activities were performed, including literature search on gadolinium chemistry, chemical precursors, sol-gel reaction strategies for alcogels, calculations of molar, weight and volumetric proportions of chemicals.

Preparation of SCM-PEG Alcogel Incorporating $Gd_2O_3$

Appropriate chemical precursors were obtained and employed according to selected sol-gel strategy and procedure to produce SCM alcogel, which incorporated $Gd_2O_3$, and bis-3-aminopropyl PEG. TEOS was used as precursor for silica instead of TBOS, and ammonium hydroxide $NH_4OH$ was used as a sol-gel catalyst at a molar ratio of 0.05M to 1M alcogel/aerogel. Additional amounts of $NH_4OH$ were added as required by other reactions in the system. 7.5 grams of bis (3-aminopropyl)polyethylene glycol and 0.4 grams of $GdCl_3$ were dissolved and mixed with 15 ml TEOS and other precursors in ethanol, and the sol-gel procedure continued. Shortly after completing the sol-gel procedure, a soft gel formed with a liquid layer on top. After three days at room temperature, this liquid layer also formed soft gel, which was thoroughly mixed with bulk of soft gel.

Removal of Reactions Byproducts, Surface Adsorption of Aminopropyl PEG, and Preparation of Micro Gel Particles These three (3) processes were conveniently performed simultaneously in one procedure. 7.5 grams of aminopropyl PEG were dissolved in 200 ml ethanol. The soft gel was washed in 3× volume ethanol to remove by reaction products and to enable the adsorption of amino-PEG by the alcogel, while being stirred at a high speed to form micro particles. Excess ethanol solution was decanted off, and the particles were taken to autoclave drying. Addition of anionic dispersants, such as, sodium hexa-meta-phosphate @ 400-500 ppm in suspending liquid at pH8, helped to reduce final aerogel nano particle size from 60% but larger than 2.0 μm (up to 20 μm) and 40% less than 2.0 μm to all below 3-6 μm. After further dispersion of dry aerogel particle with ultrasonic vibration most of the de-aggregated particles were below 1-0 μm. Thus, usage of anionic dispersants helps keep nano aerogel particles from re-gelling to agglomerate into larger ones.

Autoclave $CO_2$ Drying

Replacement of ethanol in alcogel by $CO_2$ was done both near critical/supercritical conditions, following findings in Task-2. However, it was later discovered that the alcogels were not completely dried, due to the presence of excess ethanol, than was in silica alcogel in Task-2. This was corrected in later runs.

Particle Dispersion and Fractionation Strategy

Micronization in ethanol with SHMP at 400 ppm and SPA at 100 ppm plus the bis-peg at a pH or 8 was used to help the particles separate instead of reverting to their natural agglomeration tendencies.

TABLE 2

Physical Properties of Nano Aerogel Particles

| Material | Density (g/cc) | Porosity (%) | BET ($m^2$/g) |
|---|---|---|---|
| SCM-A | 0.12 | 94.77 | 333.1 |
| 2A: SCM-Gd-PEG* | 0.26 | 88.38 | — |
| 2D: SCM-Gd (NO PEG) | 0.16 | 92.72 | — |

*Used in 'Seek & Destroy' Control Release Therapy

Abbreviation Key

SCM: Silicon oxide-Calcium oxide-Magnesium oxide

A: Autoclaved

Gd: Gadolinium Oxide

PEG: Polyethylene Glycol

Example 3

Drugs and Biologics Encapsulation in PEG Aerogel

Paclitaxel Encapsulation:

Paclitaxel Injection USP, undiluted 100 mg solution containing 16.7 mg Paclitaxel [Bedford Laboratories, Bedford, Ohio] was used in encapsulation/loading test. Each 1 ml solution contains 6 mg Paclitaxel, 527 mg polyethoxylated castor oil, and 49.7% v/v dehydrated alcohol. 5 ml (=2.6 g) granules from PEG aerogel #2 (2009 cold preparation) were desiccated overnight to remove any absorbed vapors during storage. 3 ml [2.4 g] of undiluted Paclitaxel solution were added gradually to PEG aerogel granules and were almost immediately absorbed into the aerogel granules in less than a minute. The loaded aerogel granules [slightly sticky] were stored in a small-capped glass bottle in a glove box.

Gemcitabine HCL [Gemzar] Encapsulation

Gemzar [Eli Lilly, Indiana] solution was made by dissolving 200 mg Gemcitabine HCl in 5 ml 0.9% NaCl [sodium chloride] aqueous solution. 2.3 ml (0.61 g) PEG aerogel #1 ["hot" preparation, 2009] granules were desiccated overnight to remove any absorbed vapors during storage. 1.8 ml of Gemcitabine HCl solution was added to the aerogel granules gradually with immediately absorbed. However, after 10 minutes, PEG granules started to dissolve [melt together]. The mixture was placed in a desiccator to remove excess water and render dry loaded aerogel granules.

Encapsulation of Large Biologics: BSA Protein

BSA protein (MW=66,000) was used as an example of large biologic molecules to be encapsulated in PEG aerogel during the gelation process. The encapsulation method is described in the aerogel preparation section.

The results of drug and biologics encapsulation in PEG aerogel granules are shown in Table 3 below.

TABLE 3

Drug Loading and Biologics Encapsulation in PEG Aerogel Granules

| Drug/Biologic | Aerogel Density (g/cc) | Aerogel Porosity (vol %) | Loading/ Encapsulation (mg/ml Aerogel) | Loading/ Encapsulation (mg/g Aerogel) |
|---|---|---|---|---|
| Paclitaxel Solution | 0.52 | 57% | 480 | 923 |
| Gemzar Solution | 0.265 | 78% | 821 | 3098 |
| BSA Protein | 0.30 | 75% | 23 | 77 |

Example 4

Drug Release from PEG Areogel

Paclitaxel Release Procedure

Since Paclitaxel solution is soluble in ethanol and PEG aerogel is not soluble in ethanol, placing weighed Paclitaxel-loaded PEG aerogel granules in ethanol, and measuring weight loss of aerogel solid as a function of time, provided a convenient and simple method for measuring Paclitaxel release behavior from PEG aerogel at room temperature. Release tests were conducted using a discrete sample of loaded aerogel granules for each test [each is 100 mg±10 mg] and measuring weight loss due to Paclitaxel solution release into 10 ml anhydrous ethanol liquid. After a pre-determined time period, PEG aerogel granules were separated from ethanol and dried in a desiccator for at least one hour. The final weight of dried aerogel granules was measured and net weight loss was calculated. Correction for weight loss from evaporation of Paclitaxel solution alcohol [not used in release test] during same period of drying were made. Paclitaxel injection solution at 100 mg/16.7 ml (supplied by Bedford laboratories, Bedford, Ohio) was loaded into PEG aerogel at a loading rate=480 mg Paclitaxel solution/ml PEG aerogel, or 923 mg solution/1 g PEG aerogel. The release results are shown in Table 4 below.

TABLE 4

Time Release of Encapsulated Paclitaxel Solution from PEG Aerogel in Ethanol

| Release Time (minutes) | Total Encapsulated Paclitaxel (mg) | Released* Amount (mg) | Remained* Amount (mg) | Percent Released (%) | Percent Remained (%) |
|---|---|---|---|---|---|
| 15 | 52.0 | 33.5 | 18.5 | 64.4 | 35.6 |
| 30 | 52.0 | 31.8 | 20.2 | 61.2 | 38.8 |
| 45 | 56.9 | 37.5 | 19.4 | 65.9 | 34.1 |
| 60 | 47.4 | 35.9 | 11.5 | 75.7 | 24.3 |

*Corrected for weight loss of Paclitaxel solution by evaporation during drying [at 10.6% wt.]

As an example of encapsulation and release of pharmaceutical biologics, release tests conducted using one sample weighing 13 mg PEG aerogel encapsulating 1 mg BSA protein in 10 ml distilled water at room temperature. Small solution samples were withdrawn at indicated time intervals above for BSA analysis with UV-spectroscopy at 280 and 260 nm wavelength. Results are calculated and tabulated. The results of release test are shown in Table 5 below.

TABLE 5

Sequential Time Release of Bovine Serum Albumin Protein [BSA] Encapsulated in PEG Aerogel

| Release Time | Released BSA (mg) | Cumulative Release (mg) | Cumulative Percent Release (% of 1 mg) |
|---|---|---|---|
| 15 minutes | 0.19 | 0.19 | 19 |
| 3 hours | 0.22 | 0.41 | 41 |
| 20 hours | 0.26 | 0.67 | 67 |

Example 5

Development of a Delayed Release Option for PEG Aerogel

It was observed that drug release from PEG aerogel exhibit an initial fast release followed by slow release and, thus, a delayed release option may be desirable. Coating the PEG aerogel with a slowly soluble material such as gelatin would delay and slow down the drug release.

Coating of PEG Aerogel

In one coating experiment, seven pharmaceutical grade gelatin capsules [Capsugel-Pfizer] were dissolved in boiling 10 ml of distilled water and heating continued to evaporate the water volume to 5 ml. The solution was cooled briefly in a refrigerator to obtain viscous solution. One strip of PEG aerogel [8 mm×4 mm] was dipped into a small amount of the viscous solution and withdrawn and placed in desiccator to dry; single dip coating. A second strip of PEG aerogel [9 mm×4 mm] was dipped twice in the viscous solution to form a double-dip coating. No shrinkage of the aerogel strips was observed.

Testing Coated PEG Aerogel for Delayed Release

The single coated aerogel strip was placed in 40 ml distilled water at 37° C. which was gently stirred with a magnetic stirrer and dissolution and consequent PEG aerogel release into water were observed over a period of time. The dimensions of the PEG aerogel were measured from time to time to get an estimate of the amount released. The results are shown in Table 6 below.

TABLE 6

Delayed Release of Single Gelatin-Coated Peg Aerogel Granule
[8 mm × 4 mm]* in Distilled Water At 37°

| Time Period (minutes) | Peg Aerogel Release (wt-%) | Peg Aerogel Release Rate (wt-% per minute) |
|---|---|---|
| 0-8 | 0 | 0 |
| 9-33 | 37.5 | 1.5 |
| 34-50 | 62.5 | 3.68 |
| TOTAL: 50 | 100.0 | 2.0 |

*Single coating of gelatin on PEG aerogel granule [Sep. 23, 2010]. Release Test on Sep. 24, 2010.

Example 6

Protein-PEG Aerogel Surface Linkage

There are many ways for coupling proteins to PEG molecules in solutions, but a present objective is to arrive at a universal strategy for coupling all types of proteins/peptides to the outer surface of PEG aerogel, in such a manner as to leave the whole protein molecule available for its natural/normal functions. Since all proteins and peptides have an N-terminus [amine group] at one end, and a C-terminus [carboxyl group] on the other end, it seemed reasonable to effect the protein-PEG surface linkages at one of these end groups, thus leaving the whole protein chain available for its normal functioning.

The strategy used was to link the protein through the C-terminus. This C-terminus [carboxyl group] needs to activated for reactions with anchoring sites on the PEG aerogel surface, which would normally be the hydroxyl groups, forming multiple ester bonds along the aerogel surface. However, other anchoring sites may be introduced into the aerogel surface, by incorporating PEG terminated with groups such as, for example, amine, phosphate, ether, etc., to form other types of bonding with protein's C-terminus. Activation of protein C-terminus carboxyl group is achieved by several activating reagents, such as the one used in this work; EDC [1-Ethyl-3-(3-dimethylaminopropyl)carbodiimide Hydrochloride]. The mechanism of this reaction is well documented in the literature.

Preparation of Surface Linked Protein-PEG Aerogel

To ensure surface linkage between PEG aerogel and protein, solid phase reaction was adopted. Thus, to 1 ml pH 4.5-5.0 solution, 10 mg BSA protein powder was added and dissolved, then 5 mg EDC was added and dissolved, and this solution was immediately added to ~0.5 g PEG aerogel solid sheet. After 5 minutes of shaking to ensure wetting of the solid aerogel, the aerogel-solution mixture was placed in a desiccator to dry off the water overnight at room temperature while giving sufficient time for reactions to proceed. The dried product was washed in 5 ml anhydrous ethanol by vigorous shaking several minutes, then removing the ethanol to remove any loosely held unreacted BSA and reaction by-products. This washing was repeated.

It was observed that the dried aerogel-BSA "conjugate" was water insoluble even at 37° C. as shown in Table 6. The aerogel was soaked in distilled water for over 20 hours, after initial stirring for 30 minutes or more, the water was removed, and the aerogel solid was tested for amine with TNBSA. The results are shown in Table 7.

TABLE 7

Protein-PEG Aerogel Surface Linkage: Solubility of Purified
Solid Protein-PEG Conjugates in Water at Room and
Body Temperatures

| Aerogel Product | Room Temperature (23° C.) | Body Temperature (37° C.) |
|---|---|---|
| BSA-PEG | No | No |
| PEG | Yes | Yes |
| BSA-PEG-O | No | No |
| PEG-O | Yes | Yes |
| BSA-PEG-N | No | No |
| PEG-N | Yes | Yes |

Conclusion

Coating/attachment of BSA caused PEG aerogels to become water insoluble and, thus, proves the strong attachment of BSA protein onto PEG aerogel.

Possible explanations to insolubility: (a) both BSA protein and EDC [activating reagent for protein's carboxyl groups] were used in excess [≥10 folds] of what was needed for surface coverage of PEG, leading to self cross linking of protein molecules to form network with PEG surface groups; or (b) it also may be that PEG's ether oxygen got involved in reactions with protein, leading to PEG's insolubility. Excess EDC was suggested by the manufacturer, however it is expected that lesser EDC and protein would lead to lesser surface reactivity and lesser insolubility.

Colorimetric Analysis of Protein Primary Amines in BSA-PEG Aerogel "Conjugates"

TNBSA [2,4,6-Trinitrobenzene sulfonic acid] reacts with primary amino groups of amino acids in aqueous solution at pH 8 to form yellow-orange adducts. 0.5 ml of freshly diluted 0.5% TNBSA solution was added to purified solid BSA-PEG aerogel granules. The results are shown in Table 8.

TABLE 8

Protein-PEG Aerogel Surface Linkage: Qualitative Colorimetric
Analysis of Protein on Purified Solid Peg Aerogel Using TNBSA
For Primary Amine Detection

| Protein-Aerogel Conjugate | Orange-Yellow Color? | Aerogel Composition | Bond Type With Protein C-Terminus |
|---|---|---|---|
| BSA-PEG | YES* | PEG only | Ester [polyester] |
| BSA-PEG-O | YES* | PEG + Diglycidylether terminated PEG, 1000 | Ester [polyester] |
| BSA-PEG-N | YES** | PEG + Bis(3-aminopropyl) terminated PEG 1,500/2,100 | Amide & Ester [polyamide & polyester] |
| Reference Protein: BSA | YES* | — | — |

*Immediate color development at room temperature.
**Slow color development [15 minutes to 2 hours at 37 C. °].

Conclusion

The orange color proves the presence of protein in the BSA-PEG aerogel conjugates.

Note: Ellman's Reagent did not show color development with either BSA protein, nor with any BSA-PEG conjugate, indicating that there were no free sulfhydryl groups in this BSA protein sample.

While methods and compositions have been described with reference to various embodiments, those skilled in the art will understand that various changes may be made and equivalents may be substituted for elements thereof without departing from the scope and essence of the disclosure. In addition, many modifications may be made to adapt a particular situation or material to the teachings of the disclosure without departing from the essential scope thereof. Therefore, it is intended that the disclosure not be limited to the particular embodiments disclosed, but that the disclosure will include all embodiments falling within the scope of the appended claims. In this application all units are in the metric system and all amounts and percentages are by weight, unless otherwise expressly indicated. Also, all citations referred herein are expressly incorporated herein by reference.

REFERENCES

[1] DeGrado, W. F. et al. *Kinetics and mechanism of hemolysis induced by melittin and by a synthetic melittin analog.* Biophysical Journal. 1982 (37:1):329-338.

[2] Hiromi Sato & Jimmy B. Feix. *Lysine-Enriched Cecropin-Melitin Antimicrobial Peptides with Enhanced Selectivity.* Antimicrobial Agents and Chemotherapy. 2008. (52:12): 4463-4465.

[3] Immune Central. *Immune System Series: Natural Killer Cells.* http://www.immunecentral.com/immune-system/iss9.cfm. 2002.

[4] Juan Pablo Pratt[1], Dino J. Ravnic[1], Harold T. Huss[1], Xiaoqun Jiang[1], Benjamin S. Orozco[1] and Steven J. Mentzer[1] *Melittin-induced membrane permeability: A nonosmotic mechanism of cell death.* In Vitro Cellular & Developmental Biology—Animal. 2005. (41:10): 349-355.

[5] Lynch, Thomas. *Activating Mutations in the Epidermal Growth Factor Receptor Underlying Responsiveness of Non-Small-Cell Lung Cancer to Gefitinib.* (hhtp://content.nejm.org) New England Journal of Medicine. 2004.

[6] Michael J. Parr, Steven M. Ansell, Lewis S. Choi, Pieter R. Cullis. *Factors influencing the retention and chemical stability of poly(ethylene glycol)-lipid conjugates incorporated in to large unilamellar vesicles.* Biochemica et Biophysica Acta. 1994. (1195): 220-228.

[7] Reciprocal Net. *Melittin—Reciprocal Net Common Molecule.* National Science Digital Library. 2002-2009.

[8] TimTech. *Melittin.* http://www.timtec.net/. 2008.

[9] Tosteson, M. T., Tosteson D. C. *The_sting. Melittin forms channels in lipid bilayers.* Biophysical Journal. 1981 (36): 109-116.

[10] Whitehouse, David. *Sci/Tech Cancer stung by new research.* BBC News Online. 1999.

[11] Wikipedia, The Free Encyclopedia. http://en.wikipedia.org. 2009.

[12] Xia Wang, Yong Lin. *Tumor necrosis factor and cancer, buddies or foes?* Acta Pharmacologica Sinica. 2008. (11): 1275-1288.

[13] Xiang-Hong Peng, Ze-Hong Cao, Jin-Tang Xia, Grant W. Carlson, Melinda M. Lewis, William C. Wood and Lily Yang. *Real-time Detection of Gene Expression in Cancer Cells Using Molecular Beacon Imaging: New Strategies for Cancer Research.* American Association for Cancer research. 2005. (65): 1909-1917.

[14] Anthony A. Boiarski, Arfan Rampersaud, Kristie Melnik, Rob Walezak. *Private Communication & Topic #A04-187 Proposal #A043-187-2305. iMEDD, Inc.* 2004.

I claim:

1. Polyethylene glycol (PEG) aerogel particles consisting essentially of polyethylene glycol and having an average particle diameter not substantially above about 2µ, a volumetric porosity of greater than about 50%, and pore sizes capable of retaining drug molecules.

2. The PEG aerogel of claim 1, wherein said drug molecule is one or more of Paclitaxil, gemcitabine, alprostadil, amphotericin B, camptothecin, cosalane, chloramphenicol, cyclosporine, iovastatin, omeprazole, dexamethasone, HIV-1 protease inhibitors, melittin, epidermal growth factors, hydroxycortosone, indomethacin, phenytoin, and tolbutaide; insulin-5700, IgG-150,000, or an interferon.

3. The PEG aerogel of claim 1, wherein said pore sizes range from between about 2 nm and about 200 nm.

4. The PEG aerogel of claim 1, wherein volumetric porosity ranges from about greater than 50% to about 99%.

* * * * *